United States Patent [19]

Py: Daniel

[11] Patent Number: 4,908,024
[45] Date of Patent: Mar. 13, 1990

[54] OCULAR SELF-TREATMENT APPARATUS AND METHOD

[76] Inventor: Daniel Py, 22 Ferncliff Ter., Short Hills, N.J. 07078

[21] Appl. No.: 188,331

[22] Filed: May 4, 1988

[51] Int. Cl.⁴ .................................................. A61M 7/00
[52] U.S. Cl. ................................................................ 604/300
[58] Field of Search ............... 604/289, 290, 294–303; 351/158, 223

[56] References Cited

U.S. PATENT DOCUMENTS

| | | | |
|---|---|---|---|
| 2,382,771 | 8/1945 | Bowers | 604/300 |
| 2,633,122 | 3/1953 | Vannas | 604/294 |
| 3,279,466 | 10/1966 | Mings . | |
| 3,506,001 | 4/1970 | Costello | 604/294 |
| 3,913,575 | 10/1975 | Windsor | 604/300 |
| 3,934,585 | 1/1976 | Maurice | 604/302 |
| 4,085,750 | 4/1978 | Bosshold . | |
| 4,131,115 | 12/1978 | Peng . | |
| 4,344,430 | 8/1982 | Astrove | 604/300 |
| 4,386,608 | 6/1983 | Ehrlich . | |
| 4,468,103 | 8/1984 | Meckler | 604/300 |
| 4,515,295 | 5/1985 | Dougherty | 604/300 |
| 4,531,944 | 7/1985 | Bechtle . | |
| 4,543,096 | 9/1985 | Keene . | |
| 4,573,982 | 3/1986 | Forbes et al. | 604/300 |
| 4,605,398 | 8/1986 | Herrick . | |
| 4,647,165 | 3/1987 | Lewis | 351/158 |
| 4,685,906 | 8/1987 | Murphy . | |
| 4,733,802 | 3/1988 | Sheldon . | |

OTHER PUBLICATIONS

Letocha, Charles E., "Methods for Self-Administration of Eyedrops," *Ann Ophthalmol,* 17:768–769 (1985).
Sheldon, G. M., "Self-Administration of Eyuedrops," *Opthalmic Surgery,* May 1987, pp. 393–394.

*Primary Examiner*—C. Fred Rosenbaum
*Attorney, Agent, or Firm*—Kenyon & Kenyon

[57] ABSTRACT

An ocular self-treatment apparatus and self-treatment method for simplifying and improving the ease of ocular self-treatment. The apparatus is formed of a frame to be worn by the patient. The frame supports one or two light deviation apparatus. These apparatus deviate the visual access of the patient. The frame also supports one or two dispensers of ocular treatment material. A patient rotates his eye upwards and the light deviation apparatus allows him to observe the lower ocular area. The patient can then evert his lower eyelid and apply ocular treatment material to the cul-de-suc of the conjunctiva.

23 Claims, 2 Drawing Sheets

4,908,024

OCULAR SELF-TREATMENT APPARATUS AND METHOD

BACKGROUND OF THE INVENTION

This invention is directed to an apparatus and method for facilitating the self-application of liquid treatment material to an eye and, in particular, to an apparatus that effects a reorientation of the line of sight to simplify and faciltate self-application of ocular treatment or care material.

Frequently, the elderly are the recipients of ocular treatment. In general, the elderly may have poor near vision and may also suffer from tremors and finger arthritis. For this reason, when liquid medicament must be applied to the eyes of an elderly individual, it generally must be applied by a third party in 70% of all patients according to a KASS study. For that reason, such treatments often have a rather low rate of compliance despite the importance of treating eye disease with regular treatments of medication.

Self-administration of eye medicine is generally difficult or improperly administered because the patient is required to place drops of liquid medicine on the eye with accuracy and delicacy. A major difficulty is that when looking in a mirror, it is only possible to apply eye drops in the vicinity of the cornea which is the most sensitive part of the eye. An additional drawback is that when liquid is placed in the vicinity of the cornea, it is quickly eliminated through the lacrimal duct with a corresponding lack of effectiveness of the administered drug.

To eliminate the inadequacies of the conventional ocular treatment it is desirable to administer ocular treatment material in a way that the administered medication will remain in the eye and that the application is not unnecessarily unpleasant for the patient.

SUMMARY OF THE INVENTION

Generally speaking, in accordance with the invention, an ocular self-treatment apparatus and self-treatment method are provided for simplifying and improving the ease of ocular self-treatment. The device is formed of a frame to be worn by the patient. The frame supports one or two light deviation apparatus. These apparatus deviate the visual axis of the patient. The frame also supports one or two dispensers of ocular treatment material. A patient rotates his eye upwards and the light deviation apparatus allows him to observe the lower ocular area. The patient can then evert his lower eyelid and apply ocular treatment material to the cul-de-sac of the conjunctiva.

Accordingly, it is an object of this invention to provide an improved device and method for the self-administration of ocular treatment medication.

Another object of the invention is to provide an improved ocular self-treatment device and method that allows the patient to self-administer ocular treatment material even if the patient suffers from tremors.

A further object of the invention is to provide an improved ocular self-treatment device and method in which liquid ocular treatment material can be applied to the inferior conjunctival cul-de-sac.

Still another object of the invention is to provide an improved ocular self-treatment device and method in which the user can observe the application of ocular treatment medication without fear of injuring his eye.

Still other objects and advantages of the invention will in part be obvious and will in part be apparent from the specification and the drawings.

The invention accordingly comprises the features of construction, combinations of elements, and arrangements of parts which will be exemplified in the constructions hereinafter set forth, and the scope of the invention will be indicated in the claims.

BRIEF DESCRIPTION OF THE DRAWINGS

For a fuller understranding of the invention, reference is had to the following description taken in connection with the accompanying drawings, in which.

DETAILED DESCRIPTION OF THE PREFERRED EMBODIMENTS

Figure 1:
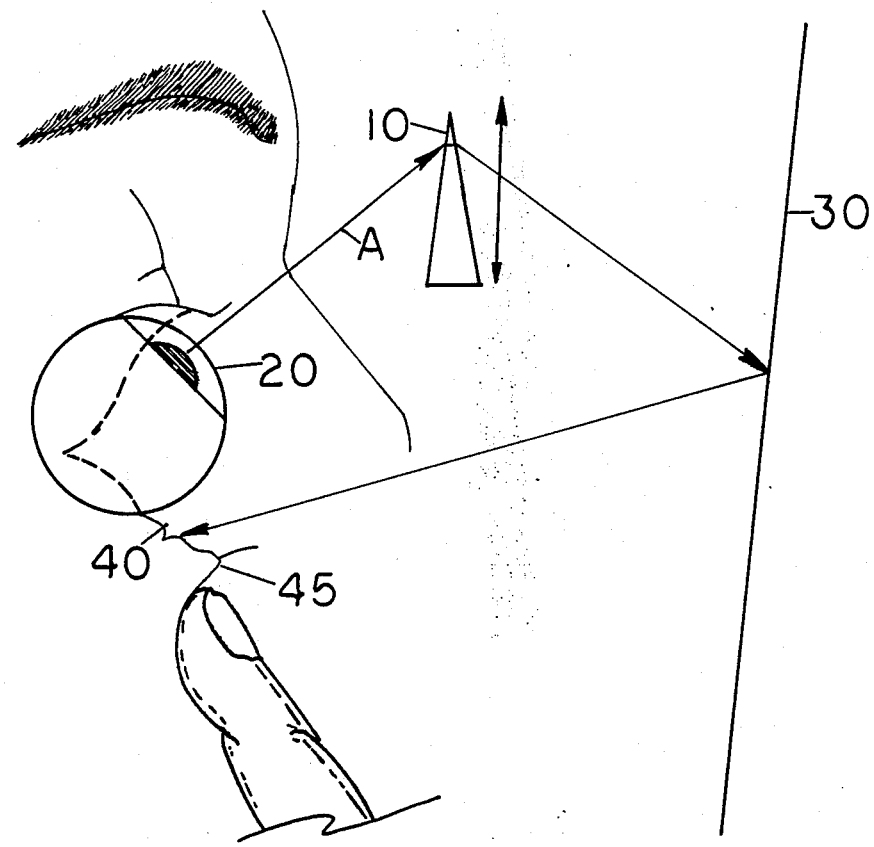
FIG. 1 is a diagrammatic view illustrating the effect of the instant invention.

FIG. 1 is a diagrammatic illustration of the deviation or refraction of a visual beam by interposing a prism 10, of appropriate angular deviation, in a patient's line of sight A, between a pupil 20, of a pateient's eye and a mirror 30. Deviating the line of sight, as shown in FIG. 1, allows the patient to directly observe the area of the inferior conjunctival cul-de-sac 40. The cul-de-sac region is uncovered if the eyeball is rotated upwards prior to everting the lower eyelid 45. By deviating the line of light, utilizing prism 10, a patient can ensure that he has properly everted his lower eyelid 45 to expose cul-de-sac 40 and has also ensured that the medication flows to cul-de-sac 40.

Figure 2:
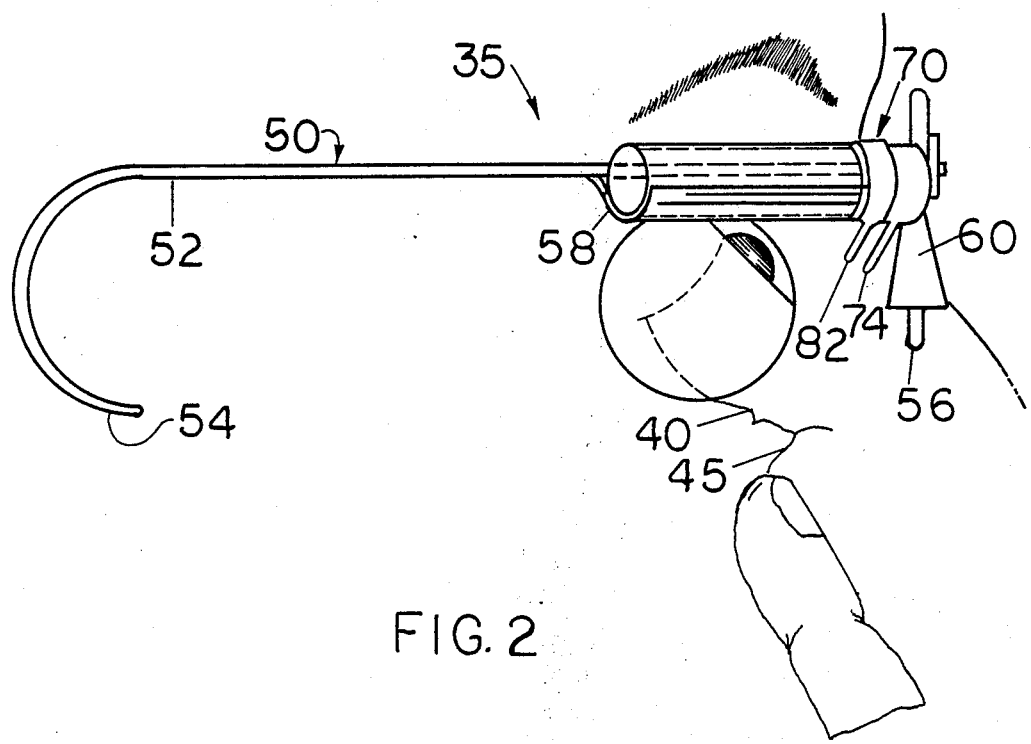
FIG. 2 is a diagrammatic view illustrating a patient wearing an ocular self-treatment device constructed in accordance with a preferred embodiment of the instant invention.

Referring generally to FIG. 2, a patient wearing an ocular self-treatment apparatus, constructed in accordance with a preferred embodiment of the present invention, is depicated generally at 35. Apparatus 35 includes a support frame, indicated generally at 50. Frame 50 includes a pair of temple rods 52 (one shown). Each temple rod includes an ear hook 54 for supporting and for steadying apparatus 35. Frame 50 also includes a bridge 56 to rest and steady frame 50 on the nose of the patient. To divert the line of sight and allow a patient to observe the area of the conjunctival cul-de-sac 40, frame 50 supports a pair of prismatic lenses 60 (one shown). Together, prismatic lenses 60 and frame 50 form a pair of prismatic spectacles.

Figure 3:
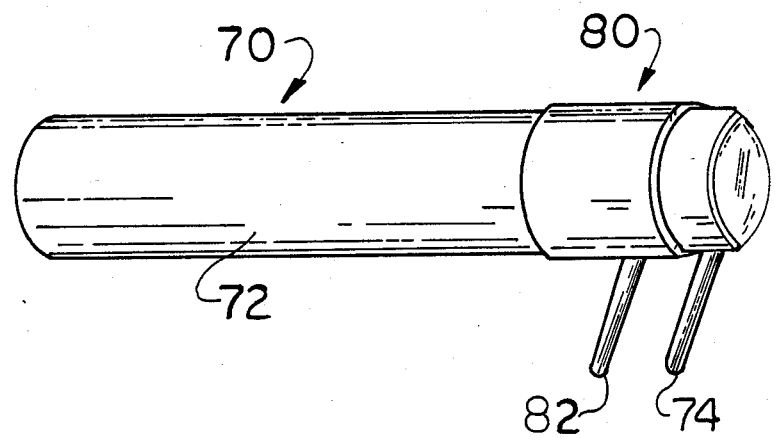
FIG. 3 is a perspective view of a container for occular treatment material constructed in accordance with a preferred emobdiment of the invention.

Ocular treatment material is stored in a dispenser, indicated generally at 70, in FIGS. 2 and 3, with similar structures identically numbered. Ocular treatment material is stored in a reservoir 72 of dispenser 70. The material stored in reservoir 72 is administered to the eye through a nozzle 74. Either temple rod 52 or both temple rods 52 support a semicylindrical dispenser support tray 58 for removably mounting dispenser 70 on frame 50.

To aid a patient in viewing ocular cul-de-sac region 40, dispenser 70 further includes a light source 80 and a lighting directing tip 82 for directing a beam of light. Lighting tip 82 is directed approximately parallel with nozzle 74. As shown in FIG. 2, the dispenser 70 is mounted on semi-cylindrical tray 58 such that both nozzle 74 and lighting tip 82 point towards inferior conjunctival cul-de-sac 40.

Ocular treatment material from dispenser 70 can be delivered to ocular cul-de-sac 40 by any appropriate method such as drops falling by gravity. In a preferred embodiment, reservoir 72 can be a pressurized container fitted with an appropriate valve through which to deliver the ocular treatment material. Alternatively, dispenser 70 can be fitted with a micro pump for delivering the ocular treatment material. Nozzle 74 can be either fixed or adjustable.

Figure 4:
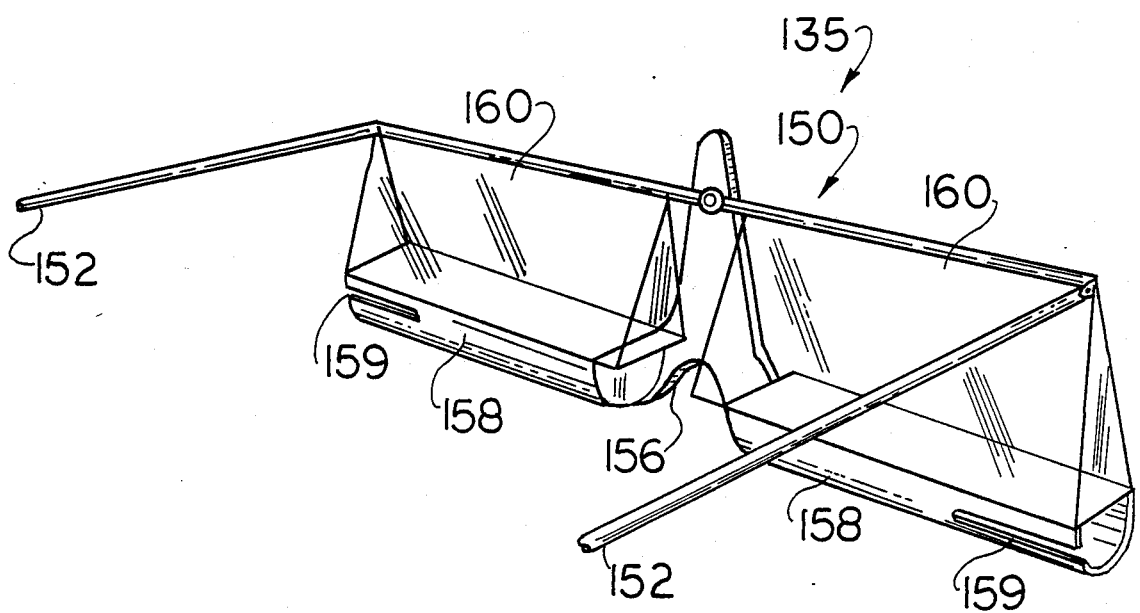
FIG. 4 is a perspective view illustrating an occular self-treatment device constructed in accordance with an alternate embodiment of the instant invention.

FIG. 4 illustrates a second preferred embodiment of the invention, like reference numerals with the prefix 1 being used to refer to similar elements. Thus, the embodiment illustrated in FIG. 4 includes a frame, indicated generally at 150. Frame 150 includes a pair of temple rods 152 and a bridge 156 to support ocular self-treatment device 135 on the head of the patient. Device 135 is fitted with prismatic lenses 160.

Ocular treatment material dispenser 70 is not mounted on temple rod 152 in this embodiment. Rather, dispenser supports 158 are provided below each prismatic lens 160. Each dispenser support 158 includes a slot 159 provided therein. When dispenser 70 is inserted within dispenser support 158, nozzle 74 and lighting tip 82 protrude through slot 159. In this manner, nozzle 74 and lighting tip 82 point towards the inferior conjunctival cul-de-sac.

Accordingly, the instant invention provides a device to aid in the self-administration of ocular treatment material. A device constructed according to the invention allows a deviation of the visual beam by the use of an appropriate light deviation apparatus, such as a prism. By diverting the visual beam, a patient can observe portions of the eye below the cornea area. Specifically, a patient can observe the area of the inferfior conjunctival cul-de-sac, an area of low sensitivity. The cul-de-sac can receive one or two drops of eye treatment fluid without spillage. Because this area has a reduced turn-over of tears, medication placed in this area will be discharged at a slower rate than if such medication is applied to any other area of the eye. Accordingly, the effectiveness of the medication is increased.

To self-administer eye treatment material, employing the device of the present invention, an individual can rest the bridge on his nose and can further place ear hooks 54 around his ears. Prism 60 or 160 is thereby positioned so that a user will peer upwards to observe the lower occular region. The user then everts lower eyelid 45 with his finger and expose cul-de-sac 40. Medication is then dispensed to cul-de-sac 40.

It will thus be seen that the objects set forth above, and those made apparent from the proceeding description, are efficiently attained and, since certain changes may be made in the above construction without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention, which as a matter of language, might be said to fall therebetween.

I claim:

1. A device for the self-administration of ocular treatment material, comprising:
   a frame, deviation means for deviating the visual axis including at least one prism positioned on the frame so that a user would rotate his eye upwards when using the device, and dispenser means for storing and dispensing ocular treatment material to the eye area, supported by the frame.
2. The device of claim 1, wherein the frame includes bridge means for resting the device on and steadying the device with a nose.
3. The device of claim 1, wherein the frame includes ear hook means for resting the device on and steadying the device with an ear.
4. The device of claim 1, wherein the dispenser means includes pump means for causing the flow of ocular treatment material.
5. The device of claim 1, wherein the dispenser means includes a pressurized canister.
6. The device of claim 1, wherein the dispenser means includes an adjustable nozzle.
7. The device of claim 1, said device further including light means coupled to said frame for illuminating the region of the eye area upon which it is desired to apply ocular treatment material.
8. The device of claim 1, wherein the prism is positioned on the frame and the frame is constructed so that when a user peers upwards, through the prism, into a mirror, a user will observe the area below the cornea and a user's eye will thereby be rotated sufficiently upwards so that the inferior conjunctival cul-de-sac can be exposed.
9. The device of claim 1, wherein
   the frame includes bridge means for resting the device on and steadying the device with a nose, and ear hook means for resting the device on and steadying the device with at least one ear, the ear hook means being coupled to the bridge means.
10. The device of claim 9, wherein
    the ear hook means includes two temple rods, each of the temple rods being coupled on one end to the bridge means, and each of the temple rods defining on its other end an ear hook for supporting the respective temple rod on an ear for supporting and steadying the frame with the ears.
11. The device of claim 10, wherein
    the deviation means for deviating the visual axis includes two prisms, each prism being mounted to the frame on either side of the bridge means, such that when the ear hook means is supported on the ears and the bridge means is supported on the nose, each prism is positioned respectively in front of an eye so that when a user peers upwardly, through a respective prism, into a mirror, the user will observe the area below the respective cornea and the user's eye will thereby be rotated sufficiently upwards so that the inferior conjunctival cul-de-sac can be exposed for receiving ocular treatment material from the device.
12. The device of claim 9, wherein
    the dispenser means includes at least one dispenser for holding ocular treatment material and having a nozzle for dispensing ocular treatment material, the dispenser being mounted to the frame and positioned such that when the ear hook means is supported on the ears and the bridge means is supported on the nose, the dispenser is located adjacent to an eye for dispensing ocular treatment material through the nozzle and into the eye.

13. The device of claim 12, wherein
the dispenser means includes two dispensers, each dispenser being mounted to the frame and positioned so that when the ear hook means is supported on the ears and the bridge means is supported on the nose, each dispenser is located adjacent to a respective eye for dispensing ocular treatment material through its nozzle and into the eye.

14. An ocular self-treatment device, comprising:
a prism constructed and angled so that if a user looks upwards, through the prism, into a mirror, the user will observe the eye region below the cornea and dispenser means coupled to the prism, the dispenser means for dispensing eye treatment material.

15. The ocular treatment device of claim 14, wherein the dispenser means includes a pressurized canister.

16. The ocular treatment device of claim 14, wherein the dispenser means includes a micro pump.

17. The ocular treatment device of claim 14, further including lighting means, coupled to the prism for illuminating the lower eye region.

18. A method for the self-administration of ocular treatment material, comprising:
peering upwards through a prism, the prism constructed so that when a user peers upwards through the prism into a mirror, the user can observe the eye region below the cornea; everting the lower eyelid to expose the ocular cul-de-sac; and applying eye treatment material to the ocular cul-de-sac.

19. The method for the self-administration of ocular treatment material of claim 15, wherein a reservoir for storing and dispensing ocular treatment material, is coupled to the prism.

20. An ocular self-treatment method, comprising:
rotating an eyeball upwards, deviating the line of sight of the eyeball with a light deviation means, wherein the light deviation means includes a prism, everting the lower eyelid of the eyeball to expose the conjunctival cul-de-sac and applying ocular treatment material to the conjunctival cul-de-sac.

21. The ocular self-treatment method of claim 20, wherein the light deviation means further includes a mirror.

22. The ocular self-treatment method of claim 20, wherein the ocular treatment material is applied from a pressurized canister.

23. The ocular self-treatment method of claim 20, wherein in the ocular treatment material is applied from a pump.

* * * * *